United States Patent
Laser et al.

[11] Patent Number: 5,667,475
[45] Date of Patent: Sep. 16, 1997

[54] ENDOSCOPIC DEVICE

[75] Inventors: Helmut Laser, Berlin; Gerald Hauer, Weilheim, both of Germany

[73] Assignee: ETB Endoskopische Technik GmbH Berlin, Berlin, Germany

[21] Appl. No.: 495,492

[22] PCT Filed: Nov. 28, 1994

[86] PCT No.: PCT/DE94/01401

§ 371 Date: Jul. 27, 1995

§ 102(e) Date: Jul. 27, 1995

[87] PCT Pub. No.: WO95/14425

PCT Pub. Date: Jun. 1, 1995

[51] Int. Cl.$^6$ .......................................... A61B 1/00
[52] U.S. Cl. .................. 600/127; 600/128; 600/131; 600/171
[58] Field of Search .......................... 600/109, 112, 600/127, 131–133, 136, 138, 160, 171, 176, 178, 179, 182, 183, 128

[56] References Cited

U.S. PATENT DOCUMENTS

| | | | |
|---|---|---|---|
| 2,235,979 | 3/1941 | Brown | 600/178 |
| 3,481,325 | 12/1969 | Glassman . | |
| 3,643,653 | 2/1972 | Takahashi et al. | 600/129 |
| 3,835,841 | 9/1974 | Terada | 600/171 X |
| 4,667,656 | 5/1987 | Yabe | 600/109 |
| 4,825,259 | 4/1989 | Barry, Jr. | 600/127 X |
| 4,850,342 | 7/1989 | Hashiguchi et al. | 600/171 |
| 4,858,001 | 8/1989 | Milbank et al. | 600/133 X |

FOREIGN PATENT DOCUMENTS

| | | |
|---|---|---|
| 0369936 | 5/1990 | European Pat. Off. . |
| 0497347A2 | 8/1992 | European Pat. Off. . |
| 0585826A1 | 3/1994 | European Pat. Off. . |
| 916999 | 12/1946 | France ........................ 600/179 |
| 2212132 | 7/1974 | France . |
| 4105634 | 4/1992 | Japan ........................ 600/171 |

OTHER PUBLICATIONS

PHLEBOLOGIE—Neue Ergebnisse der endoskopischen subfaszialen Perforansdissektion by M. Jugenheimer et al.; Aug. 1992.

*Primary Examiner*—Richard J. Apley
*Assistant Examiner*—David R. Risley
*Attorney, Agent, or Firm*—Jordan and Hamburg

[57] ABSTRACT

An instrument for endoscopic subfascial discission of perforans veins (ESDP) consists of a surgical endoscope (1) and a tube (9). The surgical endoscope (1) contains an optical image recording and transmission system, a fiber-optic lighting system and a working channel (4). A lateral handle (14) forms in an obtuse angle with the surgical endoscope and has at least one reproduction and lighting system (8, 6) guided to coupling spots (5, 7) provided at the proximal end of tube instrument. The distal end of the tube (9) extends beyond the distal end of be surgical endoscope (1) and is designed as a thicker, atraumatic lip (10) that contains a suction channel (12) diametrically arranged to a front lens system (16) and connected through a space (11) between the shaft (2) and the tube (9) to a connection fitting (13) for a suction hose (15).

11 Claims, 2 Drawing Sheets

ENDOSCOPIC DEVICE

BACKGROUND OF THE INVENTION

The invention relates to an endoscopic device, in particular to an instrument for endoscopic subfascial discision of perforans veins (ESDP). About 10% to 15% of the adult suffer from a distinct varix of the lower extremities, up to 16% of these patients have insufficient perforans veins. In the course of the medical treatment of a primary varix and of trophic skin disorders due to a post-thrombosis or to a varix these insufficient perforans veins are subfascially eliminated. In the course thereof the previous surgical methods require an extended uncovering of the perforans veins and very often suffered from post-surgical wound healing troubles or they are disadvantageous due to low precision.

In the course of the Minimal Invasion Surgery the endoscopic subfascial discision of perforans veins (ESDP) was developed by Dr. G. Hauer which is up to now considered as the most effective therapeutical principle. The instruments developed in connection with the aforesaid (refer to Jugenheimer, M; Junginger, Th.: *PHLEBOLOGY,* 4th. annual 8/92, p. 540ff.) comprises cold light operation robes of different diameter, a conventional laparoscope and accessories such as bi-polar coagulation forceps and endoscopic scissors. These standard components from different fields of endoscopy have only slightly been modified so that the instrumentation naturally shows a number of essential disadvantages. A later installed means for locking the instruments to the surgical laparoscope was not very successful in practice. A simultaneous working with the tube, the endoscope, and with the instrument just in use requires the helping hand of an assistant. For the comparatively power consuming manipulation of the tube the handle thereof is considered as being not stable enough. An essential disadvantage is the insufficient quality of the optical system of the surgical laparoscope, the low aperture of which sometimes renders the reproduction by conventional CCD—endo-cameras questionable due to the poor illumination conditions at the surgical situs (high absorption by severe bleeding). The direction of sight which usually is 5° to 10° with surgical laparoscopes generally does not ensure a sufficient sight of the instrument inserted. The manipulation is additionally impeded by the equipment lines for the camera, the high frequency devices, the fiber-optical illumination means, and for the coagulation gas exhaust which run in different directions relative to the axis of instrument.

SUMMARY OF THE INVENTION

It is an object of the present invention to provide an endoscopic device, particularly for the ESDP which is best suited for the medical procedure and which obviates the disadvantages of the previous devices mentioned hereinabove.

The object is realized by the features specified in the first claim.

BRIEF DESCRIPTIONS OF THE INVENTION

The invention will be explained in more detail in connection with the following example of embodiment, and wherein FIG. 1 shows a lateral, partially sectional view of an endoscopic device according to the invention, and FIG. 2 shows an enlarged, partially sectional, schematic view of the distal end portion of an endoscopic device according to FIG. 1.

DETAILED DESCRIPTION OF THE INVENTION

Figure 1:
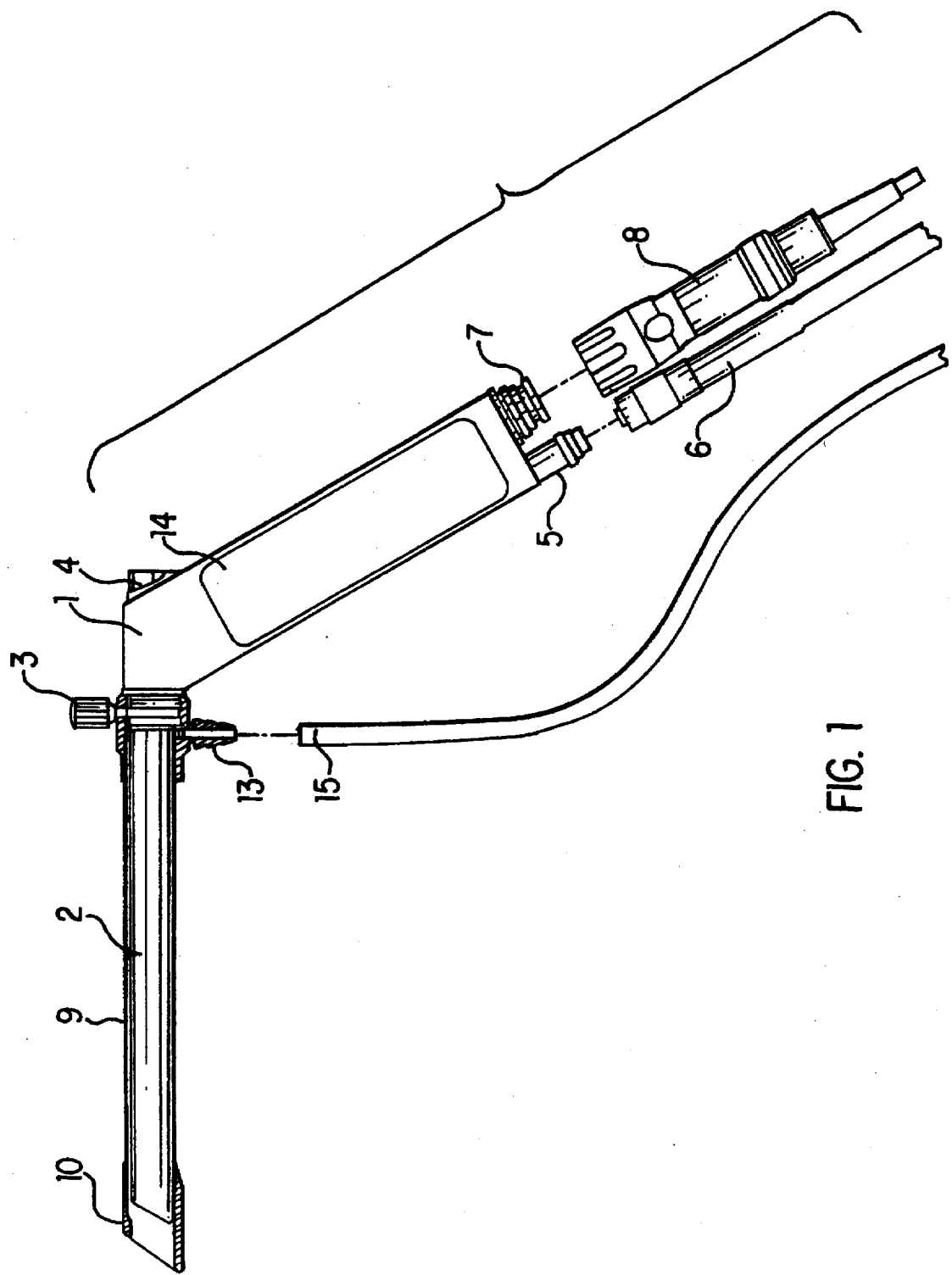
Figure 2:
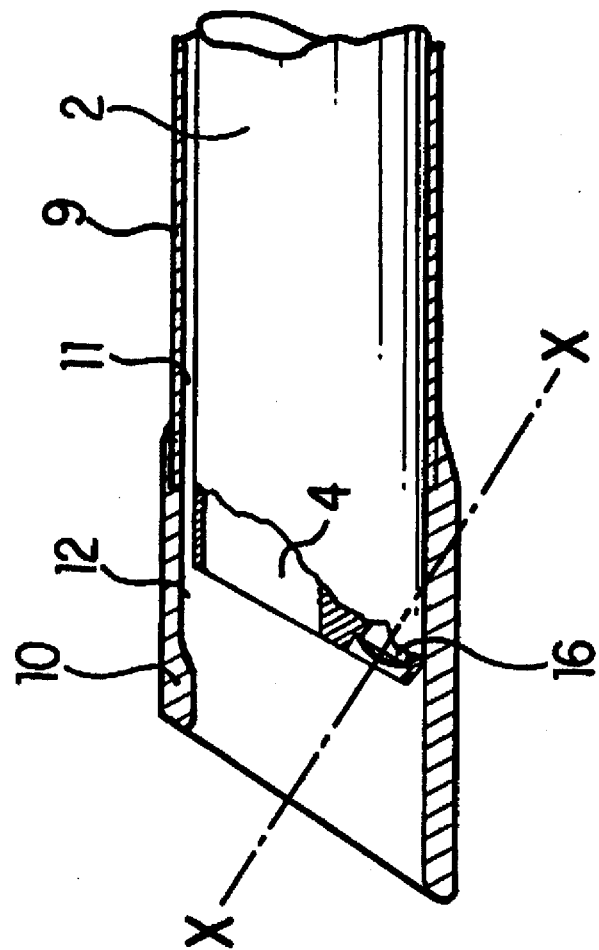

The inventional device comprises a specifically embodied surgical endoscope 1, relative to an insertable shaft 2 of which a tube 9 is lockably mounted by means of a screw 3 or any other suitable locking means. The shaft 2 of the surgical endoscope includes an optical system for image detection and transfer, fiber-optical light cables for light transmission from an external cold light source to the surgical situs, and an operation channel 4 for insertion of surgical instruments such as endoscopic knives, scissors or instruments for the surgical high frequency surgery. A handle 14 provided at the proximal end portion of the device permits operation of the device with an adequate amount of manual power. The illumination system and the optical imaging system run after a bend within the interior of the handle 14 to the end portion of the latter, where a socket 5 and a coupling 7, respectively, permit the connection of a light cable 6 of an external cold light source and of a camera 8 for transmitting the image to a monitor, respectively. It lies within the scope of the invention to install CCD-cameras, when used, for example, in said handle. The robe 9 is locked to the shaft 2 of the surgical endoscope. The distal end portion of the tube 9 is embodied as a bulgy a-traumatic lip 10 and projects over the end portion of the shaft of the surgical endoscope. Exhaust gases or the like which, for example, occur in the event of HF-coagulation can be sucked off through an intermediate space 11 constituted by preferably different embodying the external and the internal shaft diameters. The distal end portion of the shaft is guided free from backlash in the interior of the lip 10. A channel 12 is provided on the interior lip in opposition to the operation channel of the surgical endoscope which channel establishes a lumen as junction to the intermediate space 11 required for suction. According to the invention the channel 12 is in diametral opposition to a front lens 16 and the intermediate space 11 is defined by eccentrically arranging the shaft 2 and the robe 9 substantially on the channel 12 side portion. A hose coupling 13 for connecting a suction hose 15 is arranged in a common plane with and in direction of the handle 14 which substantially eliminates any obstruction of the surgeon's work. According to the invention the optical axis X—X of a front lens and a lens system 16, respectively, is defined to include an angle of 30° relative to the central axis of the shaft 2. The inventional device is preferably but not exclusively intended for the procedure of endoscopical subfascial discision of perforans veins (ESDP). Under maintaining the same inventional setup a device also for other fields of endoscopy is provided by a simple geometrical modification, for example, by an increase of diameter for said shaft and said tube. The present invention provides a device for the ESDP procedure which permits the access to remote trophically affected sites so that wound healing disorders are substantially eliminated. Considered under an endoscopical point of view the fascia cruris can be discised completely and without any incidental wounds. The medial and dorsal groups of perforans veins of the shank are safely detected and severed, irrespective of whether or not a precise pre-surgical localizing in the case of ulcus cruris is feasible.

We claim:

1. An endoscopic device comprising:
   a surgical endoscope within a tube;
   said surgical endoscope including an optical system for detecting and transmitting images, a fiber-optical illumination system and an operation channel for axial introduction of surgical instruments to a surgical site;

said surgical endoscope being laterally provided at a proximal end portion with a handle, the handle being at an obtuse angle with said surgical endoscope and said tube, said handle (14) being provided with at least one imaging and illumination system in its interior extending to an end portion of the handle to coupling means for connecting to image reproduction equipment and a light source respectively;

said optical and illumination system including a lens system having a front lens at a distal end of said surgical endoscope;

said tube having an a-traumatic lip at a distal end thereof extending beyond the distal end of said surgical endoscope to form an open-ended tubular cavity encompassing said front lens and a distal opening of said operation channel, the a-traumatic lip having a diameter greater than a remainder of said tube;

said tube having an inner diameter greater than an outer diameter of said surgical endoscope, said surgical endoscope being eccentrically disposed with said tube to define an intermediate space therebetween; and said a-traumatic lip including a suction channel in diametral opposition to said front lens of said lens system for removal of gases away from said front lens, said suction channel communicating with said intermediate space and said intermediate space communicating with a suction coupling means arranged substantially in a plane with and in direction of said handle for connecting thereto a suction source.

2. An endoscopic device as claimed in claim 1, wherein an optical axis of said front lens is at an angle of about 30° relative to a central axis of said surgical endoscope.

3. An endoscopic device as claimed in claim 1, wherein a camera for image detection is installed within said handle.

4. An endoscopic apparatus comprising:

an endoscopic shaft having a proximate end near an operator thereof and a distal end for insertion into a patient;

said endoscopic shaft including an operating channel extending from said proximate to said distal end for receiving surgical instruments therein and introducing said surgical instruments axially at said distal end to a surgical site, optical means for illuminating an area to be operated upon and transmitting an image to an image reproduction device;

said optical means including a front lens at said distal end of said endoscopic shaft;

a tube having a larger inner diameter than an outer diameter of said endoscopic shaft, said endoscopic shaft being eccentrically disposed within said tube and defining a suction channel between said tube and said endoscopic shaft;

said tube having a circumferential ring at a distal end thereof extending beyond said distal end of said endoscopic shaft to form an open-ended tubular cavity whereby an end opening of said operating channel and said front lens are recessed within said open-ended tubular cavity from a distal end of said circumferential ring;

said circumferential ring defining a channel on an inner surface thereof communicating said open-ended tubular cavity with said suction channel; and first coupling means for connecting said suction channel to a suction source, and second coupling means for connecting said optical means to an illumination and image reproduction apparatus.

5. The endoscopic apparatus of claim 4 further comprising:

a handle disposed at the proximate end of said endoscopic shaft and at an obtuse angle relative to said endoscopic shaft; and said handle accommodating passage of said optical means therethrough to a lower end thereof whereat said second coupling means are disposed such that connections to said second coupling means extend downward away from said proximate end of said endoscopic shaft eliminating obstruction of access to said operating channel during use.

6. The endoscopic apparatus of claim 5 wherein said front lens has an optical axis at an angle of about 30° relative to a longitudinal axis of said endoscopic shaft to permit viewing of surgical instruments axially extending from said end opening of said operating channel, through said open-ended tubular cavity to an operative site at a distal end of said circumferential ring.

7. The endoscopic apparatus of claim 6 wherein said channel of said circumferential ring is disposed diametrically opposite said front lens whereby fumes generated during surgical procedures are drawn off away from said front lens and said surgical site to maintain a clear view of said surgical site.

8. The endoscopic apparatus of claim 4 wherein said front lens has an optical axis at an angle of about 30° relative to a longitudinal axis of said endoscopic shaft to permit viewing of surgical instruments axially extending from said end opening of said operating channel, through said open-ended tubular cavity to an surgical site at a distal end of said circumferential ring.

9. The endoscopic apparatus of claim 8 wherein said channel of said circumferential ring is disposed diametrically opposite said front lens whereby fumes generated during operating procedures are drawn off away from said front lens and said surgical site to maintain a clear view of said surgical site.

10. An endoscopic apparatus comprising:

an endoscopic shaft having a proximate end near an operator thereof and a distal end for insertion into a patient;

said endoscopic shaft including an operating channel extending from said proximate to said distal end for receiving operating instruments therein, optical means for illuminating an area to be operated upon and transmitting an image to an image reproduction device;

said optical means including a front lens at said distal end of said endoscopic shaft;

a tube having a larger inner diameter than an outer diameter of said endoscope shaft, said endoscope shaft being eccentrically disposed within said tube and defining a suction channel between said tube and said endoscopic shaft;

said tube having a circumferential ring at a distal end thereof extending beyond said distal end of said endoscopic shaft to form an open-ended tubular cavity whereby an end opening of said operating channel and said front lens are recessed within said open-ended tubular cavity from a distal end of said circumferential ring;

said circumferential ring defining a channel on an inner surface thereof communicating said open-ended tubular cavity with said suction channel, said channel of said circumferential ring being disposed diametrically opposite said front lens whereby fumes generated during surgical procedures are drawn off away from said front lens and a operative site to maintain a clear view of said surgical site; and first coupling means for connecting said suction channel to a suction source, and second coupling means for connecting said optical means to an illumination and image reproduction apparatus.

11. The endoscopic apparatus of claim 10 wherein said front lens has an optical axis at an angle of about 30° relative to an axis of said endoscopic shaft to permit viewing of surgical instruments axially extending from said end opening of said operating channel, through said open-ended tubular cavity to an operative site at a distal end of said circumferential ring.

* * * * *